United States Patent
Bode et al.

(10) Patent No.: US 6,821,289 B2
(45) Date of Patent: Nov. 23, 2004

(54) EFFICACY AND SAFETY OF PHOTODYNAMIC THERAPY BY MULTIPLE APPLICATION PROTOCOLS WITH PHOTOSENSITIZERS THAT SHOW EXTENDED TUMOR RETENTION

(75) Inventors: Hans-Peter Bode, Jena (DE); Volker Albrecht, Jena (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 10/396,017

(22) Filed: Mar. 25, 2003

(65) Prior Publication Data

US 2004/0193233 A1 Sep. 30, 2004

(51) Int. Cl.[7] .................................................. A61N 5/06
(52) U.S. Cl. ........................................ 607/88; 128/898
(58) Field of Search ...................... 607/88–90; 606/3–10

(56) References Cited

U.S. PATENT DOCUMENTS

| | | | |
|---|---|---|---|
| 4,957,481 A | | 9/1990 | Gatenby |
| 5,298,018 A | | 3/1994 | Narciso, Jr. |
| 5,422,362 A | | 6/1995 | Vincent et al. |
| 5,697,899 A | * | 12/1997 | Hillman et al. ............... 604/28 |
| 6,011,563 A | * | 1/2000 | Fournier et al. ............... 606/2 |
| 6,128,525 A | * | 10/2000 | Zeng et al. .................. 600/476 |
| 6,383,175 B1 | * | 5/2002 | Ii et al. .......................... 606/3 |

OTHER PUBLICATIONS

Cramers et al, "Optimisation of photodynamic therapy: the influence of photosensitizer uptake and distribution on tumor response", SPIE 1999; 4156: 63–68.

Cramers et al, "Foscan uptake and tissue distribution in relation to photodynamic efficacy", British Journ. of Cancer 2003:88:283–290.

Maeda et al, "Pheophorbide A Phototoxicity and its Application to Photoradiation Therapy of Cancer", Photomedicine and Photobiology 1987;9:45–49.

Hajri et al, "Human pancreatic carcinoma cells are sensitive to photodynamic therapy in vitro and in vivo", British Journ. of Surgery 1999;86:899–906.

Aprahamian et al, "Distribution of pheophorbide A in normal tissues and in an experimental pancreatic cancer in rats", Anti–Cancer Drug Design 1993;8:101–114.

Yano et al, "Photodynamic Therapy for Rat Pituitary Tumor in vitro and in vivo Using Pheophorbide–a and White Light", Lasers in Surgery & Med. 1991;11:174–182.

* cited by examiner

*Primary Examiner*—Roy D. Gibson
*Assistant Examiner*—Henry M Johnson, III
(74) *Attorney, Agent, or Firm*—Bolesh J. Skutnik; BJ Associates

(57) ABSTRACT

A safer, improved method of photodynamic therapy is provided for treating diseased, hyperproliferative tissue, including cancer, psoriasis, and arthritis, using multiple, sequential administrations of a photosensitizer (PS) prior to irradiation. Preferred photosensitizers are characterized by being retained in the diseased tissue for a longer time than in normal tissue. The interval between administrations is chosen to be of sufficient duration to allow the PS content of normal tissues to drop to a basal or negligible level before the next administration and before irradiation. At that time, the PS content of the diseased tissue is still high, not less than half of the initial content after the last PS administration. In this way, PDT with better selectivity for the diseased tissue is achieved. With sequential PS administrations, the PS burden on normal tissue can be kept low, so that side effects can be reduced, for example damage of the skin by sunlight or bright indoors artificial lighting. The precise durations between PS administrations and eventual irradiation vary between treatments, and are determined on an individual basis. Preferred PS for use with the present invention have a high and extended localization in tumor tissue. A preferred PS with these qualities is pheophorbide a.

22 Claims, 2 Drawing Sheets

High Tumor Selectivity by Repeat Administration of PS

EFFICACY AND SAFETY OF PHOTODYNAMIC THERAPY BY MULTIPLE APPLICATION PROTOCOLS WITH PHOTOSENSITIZERS THAT SHOW EXTENDED TUMOR RETENTION

BACKGROUND OF THE INVENTION

1. Field of the Invention

This invention relates to photodynamic therapy of malignant tumors or diseased tissue with enhanced cellular proliferation using photosensitizing agents that accumulate selectively in the diseased tissue. In particular, the present invention relates to time-separated, multiple administrations of photosensitizer to enhance accumulation of the photosensitizer in diseased tissue to improve light sensitivity in the diseased tissue (efficacy) and to enhance the safety for normal tissue.

2. Information Disclosure Statement

Photodynamic therapy (PDT) is a well-known method for treatment of cancer and other hyperproliferative diseases. Such other hyperproliferative diseases comprise the skin disease psoriasis, as well as arthritis, a chronic inflammatory disease of the joints.

In PDT, a photosensitizer (PS) is applied to the organism and is expected to accumulate in diseased hyperproliferative tissue to a greater extent than in normal tissue. This differential accumulation is due to several factors. In the blood, the PS is bound to plasma proteins to a varied extent. One of these plasma proteins is low density lipoprotein (LDL). LDL can be taken up by tumor cells, or other cells in hyperproliferative diseases to a higher extent than by normal cells. Therefore, a higher amount of PS is delivered to tumor cells or other hyperproliferating tissue. A further factor may be the altered capillary architecture in malignant tissue, leading to enhanced permeability of the capillaries. Furthermore, tumor tissue can have a lower pH than normal tissue. Low pH favors accumulation of PS with carboxylic groups, because these groups bind protons, thus leading to uncharged PS molecules that can penetrate biomembranes easier than charged PS. Another factor is decreased metabolism of the PS in malignant cells.

Differential accumulation of PS is a highly desirable goal in developing methods for PDT, because it helps to protect normal cells and tissues from damage inflicted by irradiation during PDT or, especially in case of the skin, by normal daylight or indoor artificial lighting. So far all known PS, when activated, cause damage to both healthy and diseased cells in their proximity. Thus, the ability of PS to preferentially accumulate in diseased tissue versus normal tissue is an important element of a beneficial treatment by PDT. Ideally, only malignant cells should be destroyed during PDT. The unaltered function of the surrounding normal, healthy cells and the continued presence of intact connective tissue fibers is the basis for good functional and structural (and in many cases good cosmetic) results with PDT. Absence of differential PS accumulation would result in the need for selective irradiation of the malignant cells. This is, however, generally not possible for a satisfactory treatment. Irradiation of tumors in PDT must include a safety margin around the tumor to ensure that all peripheral cancerous cells are destroyed. Furthermore, it is not possible to limit PDT effects in tissue depth exactly to the tumor. There, a safety margin is also necessary.

U.S. Pat. No. 4,957,481 describes single or multiple local administrations of a PS directly into a tumor mass for covering a larger tumor area. For multiple administrations, each administration is spatially separated, so that a specific volume of tissue is exposed to photosensitizers. This patent uses near simultaneous, spatially-separated, multiple administrations to establish and maintain a desired level of photosensitizer across a large volume of diseased tissue to achieve effective PDT treatment. It does not, however provide guidance to increase sensitivity in diseased tissue while maintaining or improving safety for normal tissue.

Another method involving repeated administrations of PS is described in U.S. Pat. No. 5,298,018, which describes the use of Photodynamic Therapy (PDT) as an adjunctive or stand alone procedure for the treatment of cardiovascular disease, specifically to prevent restenosis by blocking access of growth factor to binding sites in smooth muscle cells. The method relies on a pharmacokinetic therapy with or without light therapy, using physical or chemical interactions between the photosensitizers and muscle cells to block the binding sites independent of any light therapy. In this method, a photosensitizer is administered prior to the surgical or interventional procedure and then readministered after the procedure to replace photosensitizer which is cleared or washed out from the cells over time, thus maintaining a photosensitizer concentration in a level sufficient to block the binding sites. This method does not address how to improve efficacy of PDT treatments while maintaining or improving safety for normal tissue.

A method related to U.S. Pat. No. 5,298,018 is described in U.S. Pat. No. 5,422,362 to inhibit the development of intimal hyperplasia following angioplasty procedures. The method consists essentially of administering a green porphyrin to the subject concurrent with and following the angioplasty. Radiation activation of the green porphyrin is not a part of the method. This method therefore does not address PhotoDynamic Therapy treatments. It thus does not deal with how to improve efficacy of PDT treatments while maintaining or improving the safety for normal tissue.

A study of tissue absorption of the photosensitizer Foscan® was performed that features a double photosensitizer administration protocol. [Cramers et al, "Optimisation of photodynamic therapy: the influence of photosensitizer uptake and distribution on tumour respopse", SPIE Vol. 4156 (2001), p. 63–67; Cramers et al, "Foscan® uptake and tissue distribution in relation to photodynamic efficiency", British Journal of Cancer (2003) 88, 283–290] This study is restricted to meta-tetrahydroxyphenylchlorin (mTHPC), known as Foscan®, and relates the "pharmacokinetic and pharmacodynamic parameters for the photosensitiser Foscan to the extent of PDT damage." The distribution of Foscan in mice was measured after single and double injections of Foscan and the PDT response of tumor and cancer cells was measured. It was determined that the change in concentration in plasma was not significantly different for single and double injections, nor was the relative concentration in skin and tumor tissue significantly different after single or double injections. Thus, these articles demonstrate that essentially multiple administrations of the photosensitizer Foscan does not change the PDT effect of Foscan as compared to single administrations.

There is a need for a method to increase the concentration and selectivity of accumulation of photosensitizers in hyperproliferative or otherwise diseased tissue, both to increase the effectiveness of the treatment and more effectively protect healthy tissue from damage. The present invention addresses this need.

OBJECTIVES AND BRIEF SUMMARY OF THE INVENTION

It is an object of the present invention to provide a photodynamic therapy treatment for diseased, hyperproliferative tissues including cancer, psoriasis, arthritis and precancerous lesions, with improved efficacy and safety.

It is a further object of the present invention to provide a photodynamic therapy treatment method that produces higher and more selective concentrations of PS in diseased tissue than is possible with prior art methods.

Briefly stated, the present invention provides a safer, improved method for treating diseased, hyperproliferative tissue, including cancer, psoriasis, and arthritis, using multiple, sequential administrations of a photosensitizer (PS) prior to irradiation. Preferred photosensitizers are characterized by being retained in the diseased tissue for a longer time than in normal tissue. The interval between administrations is chosen to be of sufficient duration to allow the PS content of normal tissues to drop to a basal or negligible level before the next administration and before irradiation. At that time, the PS content of the diseased tissue is still high, not less than half of the initial content after the last PS administration. In this way, PDT with better selectivity for the diseased tissue is achieved. With sequential PS administrations, the PS burden on normal tissue can be kept low, so that side effects can be reduced, for example damage of the skin by sunlight or bright indoors artificial lighting. The precise durations between PS administrations and eventual irradiation vary between treatments, and are determined on an individual basis. Preferred PS for use with the present invention have a high and extended localization in tumor tissue. A preferred PS with these qualities is pheophorbide a.

The above, and other objects, features and advantages of the present invention will become apparent from the following description read in conjunction with the accompanying drawing.

BRIEF DESCRIPTION OF FIGURES

FIG. 1 Graphic representation of PS concentration over time in tumor and normal tissue, for example the skin, during repetitive administration of pheophorbide a.

DETAILED DESCRIPTION OF PREFERRED EMBODIMENTS

Figure 1:
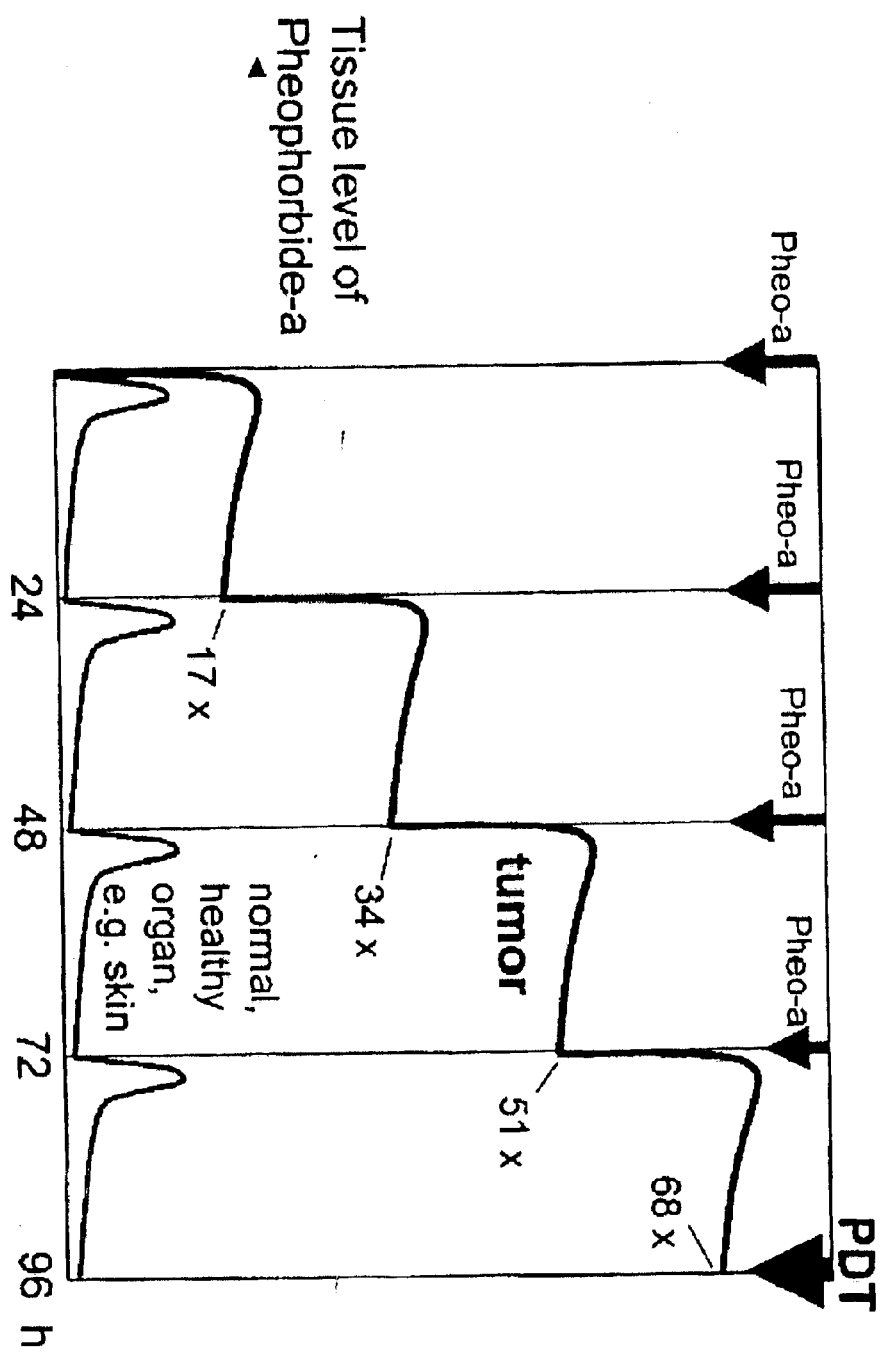
Figure 2:
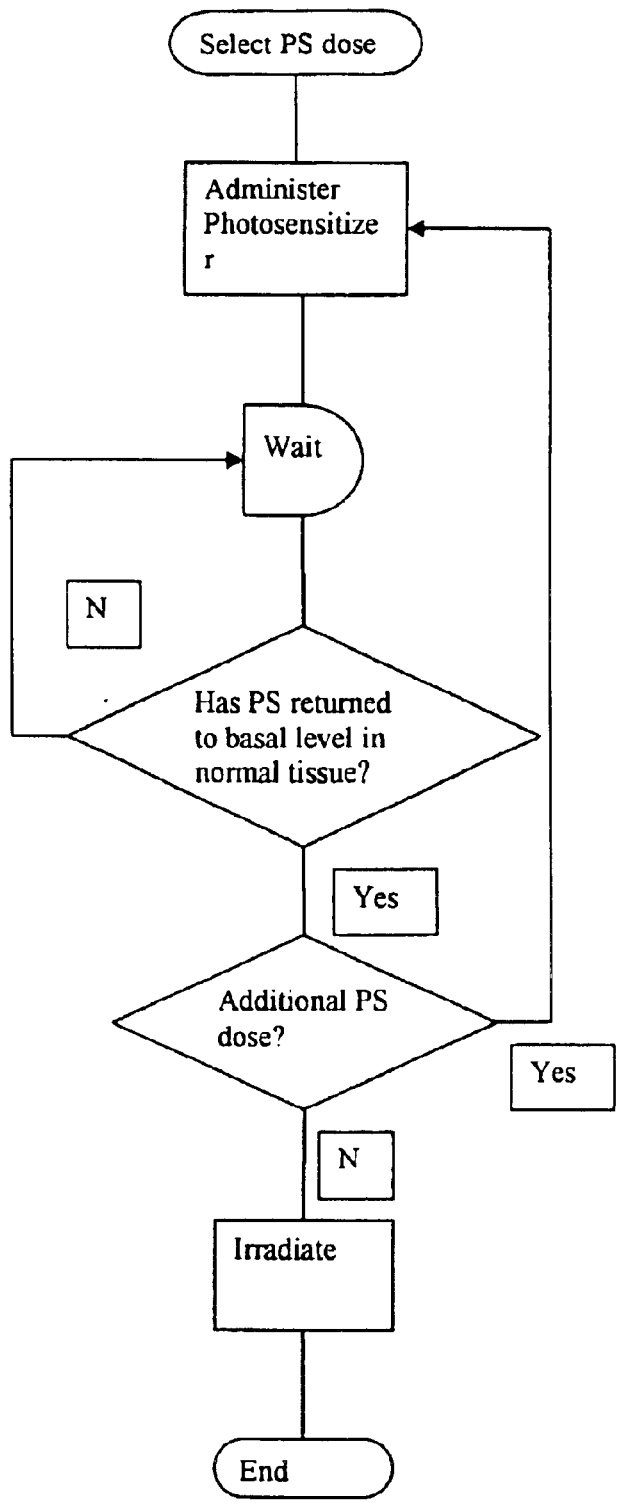
FIG. 2 A flow chart of the process for repeated administration of photosensitizer according to a preferred embodiment of the present invention.

Photodynamic therapy (PDT) of malignant tumors in principle has become a therapeutic option. However, the currently available approved photosensitizers such as Photofrin and the prodrug 5-ALA are partly unsatisfactory. This invention describes improvements of PDT with photosensitizers (PS) that show highly extended retention in tumor tissue in comparison to normal tissue. It is described how multiple, sequential administrations of such PS before irradiation can lead to enhanced PS-in-tumor concentrations in relation to normal tissue, or, alternatively, can minimize peak PS concentrations in normal tissue, thus reducing PDT side effects. This method is also effective for achieving a highly selective localization of a PS in a tumor or other diseased, hyperproliferative tissue, to provide a PDT treatment with relatively few side effects on healthy tissues. The method is thus a PDT treatment that is safer and more effective than prior PDT methods.

The present invention is of particular value if the irradiation during PDT cannot be limited exactly to the diseased tissue, for example in the case of interstitial PDT of tumors within the body, where placement of the light delivering fibres may be difficult, or where irradiation beyond the periphery of the tumor is necessary to ensure that all diseased cells are destroyed. Increased selectivity is also valuable for decreasing side-effects because of a lower or negligible amount of PS that is retained in healthy tissue. This is important for reducing photosensitization after systemic application especially of the skin, where the skin becomes susceptible to damage by sunlight or bright indoor lights for long periods after treatment. Lower concentrations in healthy tissue means less damage to healthy tissue both during and after treatment.

Many PS have a similar rate of accumulation in diseased versus normal tissue. PS can, however, also display different accumulation rates in these two types of tissue. This is especially likely if cellular metabolism of the PS is very much decreased in tumor cells or cells of otherwise hyperproliferative tissues. The decrease in tumor cell PS content then would lag behind that of normal cells. In such a case the difference in PS accumulation between diseased and normal tissue can be further increased by repetitive administration of the PS. After the first application of PS, a period of time is allowed to elapse during which the PS level in healthy tissues, for example in the skin, reaches a basal or negligible value. The tumor PS content then is still high. At this point the second PS administration is performed. The tumor PS content is increased considerably and remains high in comparison to the healthy, normal tissue, where the PS content over time returns to a basal or negligible level again. At that point the PS can be administered again and the tumor PS content is raised further. Repetitive administration with a suitable PS, with extended localization in tumor or other abnormal cells, can be used to obtain an extraordinarily high content in these non normal cells, or to obtain an extraordinarily low content in normal, healthy cells while having concentrations in the diseased tissue adequate for effect in PDT treatment. In the latter case, for example, the PS concentration in the skin can be kept low, so that the risk of skin damage by sunlight or bright artificial light is diminished.

The PS that are suitable for use with the present invention are characterized by exhibiting little change in tumor concentration after normal tissues already have largely eliminated the PS and have attained a low, basal PS content. An example of a suitable PS with extended retention in non normal cells, enabling a high differential accumulation in non normal tissue by repetitive administration, is pheophorbide a. Pheophorbide a can attain a high and extended localization in a tumor in comparison with the surrounding healthy tissue, and is thus suitable for multiple administration protocols as described here. Another example of a suitable type of PS is bacteriopheophorbide, which also can attain a relatively high and extended localization in diseased tissue.

Pheophorbide a is a naturally occurring porphyrin compound that is derived from Chlorophyll. It is generated from Chlorophyll by removal of a phytyl side chain and the central Magnesium ion. Pheophorbide a content remained high in a chemically induced rat skin tumor up to 48 hours after administration, whereas the pheophorbide a content of normal skin reached a basal value by 24 hours after administration, amounting to one tenth of the tumor-pheophorbide a content (Maeda et al, "Pheophorbide a phototoxicity and its application to photoradiation therapy of cancer", Photomedicine and Photobiology 1987, 9, 45–49). The pheophorbide a content of a xenografted human pancreatic tumor in nude mice did not decrease between 4 and 48 hours after administration, whereas the PS content of the normal skin reached a low basal value after 24 hours (Hajri et al, "Human pancreatic carcinoma cells are sensitive to photodynamic therapy in vitro and in vivo", British Journal of Surgery 1999, 86, 899–906). The pheophorbide a content of normal pancreas reached a low constant value after 24 hours while the content of a pancreatic tumor remained elevated for at least 48 hours (Aprahamian et al, "Distribution of pheophorbide a in normal tissues and in an experimental pancreatic cancer in rats", Anti-Cancer Drug Design 1993, 8, 101–114). The pheophorbide a content of a rat pituitary tumor decreased slowly during 6 hours after administration while the content of normal pituitary gland reached a basal value after 4 hours (Yano et al, "Photodynamic therapy for rat pituitary tumor in vitro and in vivo using pheophorbide a and white light", Lasers in Surgery and Medicine 1991, 11, 174–182).

In a preferred embodiment, a PS formulation is administered intravenously, although more localized administrations are contemplated. For example, for treatments such as skin tumors or psoriasis, the administrations described herein can be accomplished topically, where the PS can be incorporated into a cream or ointment and rubbed onto the affected area. Generally, the benefits of the present invention (improved efficacy and safety) are greatest for PS formulations administered intravenously or orally. However, although topical administration generally allows for greater specificity in administering PS, the present invention also improves the effectiveness of topical PDT. For example, it is often desirable to apply PS to an area greater than the area of the tumor, to ensure that any undetected diseased cells or areas are exposed and taken up by photosensitizers. In many prior art PDT applications, this increases the risk of damaging healthy tissue. The present invention, because of the resulting high specificity and low concentration of PS in healthy tissue at the time of irradiation, allows for application over a larger area without causing significant damage to healthy tissue.

The interval between administrations of PS is chosen so as to allow the PS content in normal tissue to drop to a basal value before the next administration and before eventual irradiation. A basal value means a value from where a further decrease in the PS content is much slower than the initial decrease after administration, and preferably where the tissue damage by the irradiation performed during PDT is negligible. At that time, the PS content of the diseased tissue still must be high, for example not less than half of the initial content after the last PS administration. In this way, a PDT with better selectivity for the diseased tissue is achieved. With sequential PS administrations, the PS concentration in normal tissue can be kept low, so that side effects can be reduced, for example damage of the skin by sunlight or bright indoors artificial lighting.

Before beginning PDT with a multiple administration protocol, the proper dose to be administered must first be chosen. The dose will vary according to parameters such as tissue type, disease, and photosensitizer used, and is limited by side effects that occur when the concentration of the PS after administration reaches its peak in healthy tissues. The dose is also limited by the PS uptake capacity of the tumor or other diseased tissue.

Next, the proper time interval between doses is chosen. This interval must be of a sufficient length to allow the PS concentration in healthy tissues to return to low or negligible levels. These levels should be low in comparison to the peak PS concentrations in these tissues, for example less than 20% of the peak concentration. Furthermore, the interval should be such that the concentration does not drop further considerably, for example not more than 50% during the following 24 hours. In other words, the interval should cease at a point where the photosensitizer concentration in healthy tissue is low and where the decrease in concentration has substantially leveled off. The PS level in a healthy tissue that is irradiated during a PDT should be negligible, so that the normal tissue experiences only minor detrimental photodynamic effects during photodynamic therapy. Such minor detrimental effects would be those effects to the normal tissue that are acceptable to a treating physician. In an example by analogy, minor detrimental effects can be seen in dermatological observations of minor sunburn, which results in reddening of the skin and eventual tanning, in contrast to more severe sun damage that could be accompanied by blistering or permanent toxic effects.

In some cases, an interval can be chosen where the PS level in irradiated healthy tissue is below a threshold for photodynamic effects, so that no effects occur at all in healthy tissue during irradiation. The PS concentration in irradiated healthy tissue should preferably attain a level that is below such a threshold.

After the suitable interval is chosen and has passed, a second dose of PS is administered. A third administration of the PS should be performed, if desired, when the PS content in healthy tissues, for example in that surrounding the diseased tissue, has returned to the same level as just before the second PS administration. If this does not happen, the third administration should at least be performed when PS concentration is at a low level in healthy tissues. In one example, the PS concentration at the time of the third administration should not be greater than 150% of the concentration in healthy tissue just before the second administration. The interval between the second and third PS administration should be chosen to allow for development of a significantly increased difference in PS content between diseased and healthy tissues For example, the difference in PS concentration in diseased and healthy tissue should be at least 50% higher than the difference just before the third PS administration. In the embodiment where pheophorbide a is the photosensitizer, a typical administration interval is 24 hours.

The administration can be repeated several times, preferably resulting in at least a 40:1 ratio of PS concentration in diseased tissue to PS concentration in healthy tissue.

These pharmacokinetic parameters of photosensitizer dose and interval between photosensitizer administration can be determined, for example, with a suitable animal model and can be confirmed in human studies. When treating tissues like the skin or epithelial surfaces of some internal organs, measurements of PS tissue levels can also be performed in individual patients, for example by fluorescence measurements with an optical fiber.

Where this is not possible, for example in the case of tumors within the body that will be treated with interstitial light delivery, suitable parameters for a multiple PS administration protocol are obtained from animal experiments, using a suitable model of the tumor to be treated.

In many preferred embodiments, the time period between administrations, the time period between final administration and irradiation, and each dose of PS will remain constant. There may, however, be instances where the time periods or dosage are varied, whether due to inconsistent absorption or reduction of PS in the tissue or for other reasons. These variables are determined based on the individual treatment to obtain an optimal concentration in diseased tissue and an optimal PS concentration ratio. Instances where variable time periods or doses could be useful are those instances where constant or periodic measurement of the PS concentration is feasible.

Methods of determining PS concentration are established and can be easily employed with the present invention. For example, photosensitizers are known that exhibit fluorescence at certain wavelengths and in certain percentages of concentrations. Application of fluorescence-exciting radiation can quickly reveal the concentration of PS in different body areas. Alternatively, a relatively small amount of luminescent molecules could be included in the administration. For example, photosensitizers in plasma can be detected by High Performance Liquid Chromatography (HPLC) fluorescence detection, and PS concentration can be determined in skin with a light conducting device and a fluorimeter that when put onto the skin measures reflected light.

A treatment system for regulating multiple PS administration PDT treatments is also provided in the present invention. The system comprises a radiation source and a delivery device to apply radiation to a treatment area, a regulation device to monitor the treatment and preferably control the activation of radiation so that irradiation occurs at a predetermined time based on entered protocols, and optionally an administration device to administer photosensitizers systemically or topically.

In a preferred embodiment, the regulation device is in the form of a desktop computer connected to the radiation source or a microprocessor system, with suitable software, as part of the radiation source. Such a system would also feature a display screen and input keyboard to display the treatment process and provide information about the treatment. Prior to treatment, proper dosage levels, number of administrations, and intervals between administrations and irradiation are determined. This information is then entered into the control device. A first administration is performed and the administration is automatically detected or the user indicates to the control device that the first administration has been performed. After the predetermined interval, the control device can alert the user that the second administration is due, upon which the user performs the second administration. This continues until the last administration is performed. After the predetermined interval, the control means activates the radiation source and performs the irradiation according to previously entered protocols.

In another embodiment, the control device features a safety shutter that prevents activation of the radiation source prior to expiration of the prescribed time period. This feature provides added safety by ensuring that no radiation is applied before the photosensitizer concentration in healthy tissue is at a low or basal, and thus protects healthy tissue from damage due to inadvertent radiation. In another preferred embodiment, especially in systemic administrations and in treatments where the interval between administrations is relatively short, the control device may automatically administer the photosensitizer instead of a user.

Suitable radiation delivery devices are known in the art and numerous devices exist that can be coupled to the radiation source. Such delivery device include, but are not limited to, optical fibers with or without diffuser tips, optical fiber probes and non-coherent lamps. Administration devices include syringes for systemic administration that may be usable by a medical practitioner or connected to the control device for automated PS administration.

FIG. 1 illustrates preferred intervals between administration of doses of pheophorbide a in cancerous tissue. As is shown in the figure, upon a first administration the concentration of pheophorbide a is initially high and slowly decreases. The concentration in healthy tissue quickly decreases and levels off, where at 24 hours the concentration in healthy tissue is very low and has reached a point where the concentration decreases very slowly. After the first 24 hour interval, the concentration in the tumor is 17 times that in healthy cells. The same effect is observed after the second administration of pheophorbide a. As a result, after a total of four administrations and a total time of 96 hours, the concentration of pheophorbide a in healthy tissues remains very small, and the concentration in the tumor is greater by a factor of 68.

Once the proper number of doses have been administered after the chosen intervals, the treatment area is exposed to radiation of a wavelength suitable to activate the photosensitizer. The manner of providing radiation is not limited, and will vary depending on the type and location of treatment. Examples of radiation sources include high power lamps, diode lasers, light emitting diodes, and other sources of coherent and non-coherent light. Because of the greater selectivity of photosensitizer concentration in the present invention, the area of irradiation need not be restricted strictly to a tumor area. This is an additional benefit in that any diseased or cancerous cells that are around the periphery can be destroyed without significantly harming surrounding healthy tissue, thus increasing the effectiveness of the treatment and helping to prevent reoccurrence of the disease.

The present invention is further illustrated by the following examples, but is not limited thereby.

EXAMPLE 1

PDT of a Pancreas Carcinoma.

A formulation of the PS pheophorbide a is administered intravenously 4 times as described above, with doses ranging from approximately 2 to 20 mg of PS per kilogram of body weight, achieving an at least a 50:1 ratio of PS content in the carcinoma to the PS content in the surrounding healthy pancreatic tissue. Light guiding fibres are placed within the tumor under imaging guidance. The tumor is irradiated with an energy density sufficient to necrotize the diseased tissue, preferably 100–200 $J/cm^2$, at a power density of approximately 100 $mW/cm^2$. The surrounding tissue remains intact since the photosensitizer concentration in that tissue remains under the threshold for photodynamic effects upon irradiation.

EXAMPLE 2

PDT of a Skin Tumor in a Patient That is Non-Compliant with Skin Light Protection Measures.

PS administration is split over four administrations so that after each administration only a small peak PS concentration in the normal skin is reached, achieving a better light tolerance.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A safer, improved, photodynamic-therapeutic method of treatment of hyperproliferative diseased tissue, including cancers, psoriasis, and arthritis, comprising the steps of:

a. administering a preselected dose of a photosensitizer formulation, wherein said photosensitizer is taken up by said hyperproliferative diseased tissue at a treatment site and preferentially retained in said diseased tissue over normal, healthy tissue;

b. waiting a first preselected amount of time to allow said photosensitizer to return to a basal value in normal tissue while remaining elevated in said diseased tissue;

c. administering at least one additional dose of said photosensitizer to said treatment site after said preselected first amount of time, wherein another preselected amount of time elapses between each additional dose to permit reduction of a concentration of said photosensitizer to a basal value in normal tissue; and d. irradiating said treatment site after an additional period of time has elapsed after the finally administered dose.

2. The method according to claim 1, wherein said first dose and said at least one additional dose are of an equal amount, and wherein said period of time between each administration and between a final administration and irradiation is equal.

3. The method according to claim 1, wherein said steps of administering said photosensitizer are accomplished by a method selected from the group consisting of intravenous and topical administration.

4. The method according to claim 1, wherein concentration of said photosensitizer in normal tissues returns to the same basal value after each administration, and wherein a concentration of said photosensitizer in diseased tissue remains elevated, enabling a further increase by each said administration, so that a ratio of said concentration of said photosensitizer in diseased tissue to said concentration of photosensitizer in healthy tissue increases with each said administration.

5. The method according to claim 4, wherein said basal level is such that said normal tissue experiences no photodynamic effects during said irradiation.

6. The method according to claim 4, wherein said basal level is such that said normal tissue experiences only minor detrimental photodynamic effects during irradiation.

7. The method according to claim 4, wherein said ratio is at least 40:1.

8. The method according to claim 1, wherein said photosensitizer ispheophorbide a.

9. The method according to claim 1, wherein said photosensitizer is a bacteriopheophorbide.

10. The method according to claim 1, wherein said step of irradiating is accomplished by placing at least one optical fiber into said treatment area.

11. The method according to claim 1, wherein a concentration of said photosensitizer in tissue is measured periodically or continuously.

12. The method according to claim 11, wherein said measurement is accomplished by a method selected from the group consisting of:

HPLC fluorescence detection; and administration of a preselected amount of luminescent material with said photosensitizer, followed by detection of a concentration of said luminescent material in said tissue and determination of said concentration of said photosensitizer based on relative amounts of said luminescent material and said photosensitizer administered.

13. The method according to claim 11, wherein each said period of time is selected during said treatment to ensure optimal concentration of said photosensitizer.

14. The method according to claim 1, wherein said preselected dose and period of time are determined prior to treatment by adding a step of observing the differential uptake/retention of a selected photosensitizer in human or animal subjects.

15. A device for multiple photosensitizer administration photodynamic therapy of hyperproliferative diseased tissue, including cancer, comprising:

a radiation source;

means to deliver radiation from said source to a treatment area; and means to regulate administration of multiple photosensitizer doses and to regulate said radiation delivery means based on preselected parameters; and wherein said parameters comprise the following, a number of photosensitizer administrations, period of time between said photosensitizer administrations, and period of time between a final photosensitizer administration and irradiation.

16. The device according to claim 15, wherein said regulation means alerts a user when said period of time expires and said photosensitizer administration is to be performed.

17. The device according to claim 15, further comprising means to administer photosensitizers to said treatment area.

18. The device according to claim 15, wherein said preselected parameters further comprise photosensitizer dosage, radiation power, and duration of radiation.

19. The device according to claim 15, wherein said regulation means comprises a microprocessor and suitable software.

20. The device according to claim 19, wherein said microprocessor and suitable software can automatically administer doses of said photosensitizer and deliver said radiation.

21. The device according to claim 15, further comprising means to measure a concentration of said photosensitizer in said tissue.

22. The device according to claim 21, wherein said measurement means can measure said concentration in both healthy and said diseased tissue.

* * * * *